(12) United States Patent
Epitropoulos

(10) Patent No.: US 9,179,835 B2
(45) Date of Patent: Nov. 10, 2015

(54) BINOCULAR GLARE TESTING DEVICES

(71) Applicant: Epico, LLC, Columbus, OH (US)

(72) Inventor: Alice Epitropoulos, Columbus, OH (US)

( * ) Notice: Subject to any disclaimer, the term of this patent is extended or adjusted under 35 U.S.C. 154(b) by 31 days.

(21) Appl. No.: 14/246,710

(22) Filed: Apr. 7, 2014

(65) Prior Publication Data

US 2014/0340643 A1    Nov. 20, 2014

Related U.S. Application Data

(63) Continuation of application No. 13/204,080, filed on Aug. 5, 2011, now Pat. No. 8,690,332.

(60) Provisional application No. 61/455,144, filed on Oct. 15, 2010.

(51) Int. Cl.
| | |
|---|---|
| *A61B 3/02* | (2006.01) |
| *A61B 3/028* | (2006.01) |
| *A61B 3/06* | (2006.01) |
| *A61B 3/00* | (2006.01) |

(52) U.S. Cl.
CPC ............. *A61B 3/0285* (2013.01); *A61B 3/0008* (2013.01); *A61B 3/063* (2013.01)

(58) Field of Classification Search
CPC ............................ A61B 3/0008; A61B 3/0285
USPC .................. 351/222, 234, 239, 243, 244, 246
See application file for complete search history.

(56) References Cited

U.S. PATENT DOCUMENTS

| | | | | |
|---|---|---|---|---|
| 4,861,156 | A * | 8/1989 | Terry | 351/243 |
| 5,671,039 | A * | 9/1997 | Grolman | 351/243 |
| 7,156,517 | B2 * | 1/2007 | Hosoi | 351/222 |
| 8,690,332 | B2 * | 4/2014 | Epitropoulos | 351/222 |

\* cited by examiner

*Primary Examiner* — Huy K Mai
(74) *Attorney, Agent, or Firm* — Dale F. Regelman; Quarles & Brady LLP

(57) ABSTRACT

The present invention is a glare tester attachment for use with a phoropter, comprising a pair of eye cups, both eye cups each comprising a wall partially enclosing a hollow interior chamber and having a viewing aperture defining a respective viewing line of sight axis for each eye cup, a portion of each wall being provided with a plurality of lights disposed around said line of sight axis. The invention may be incorporated into a phoropter or a hand-held device.

20 Claims, 18 Drawing Sheets

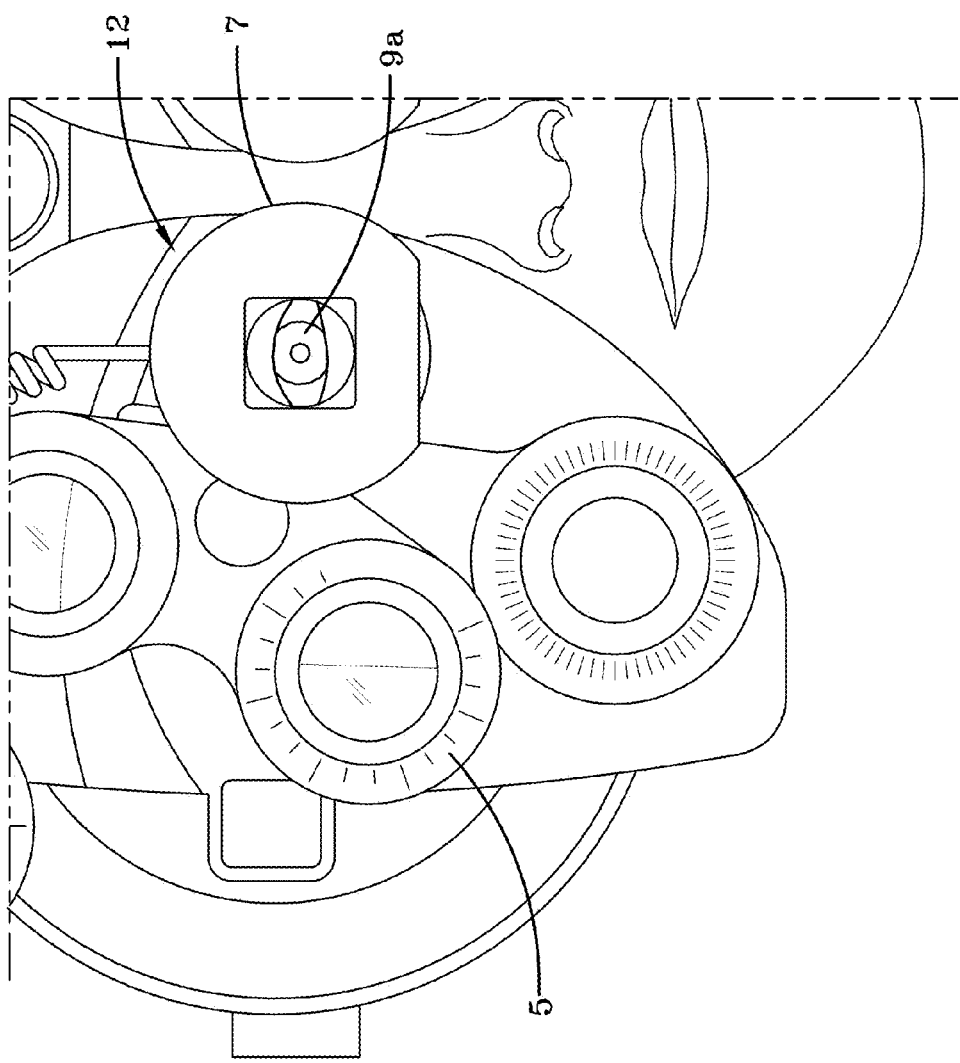

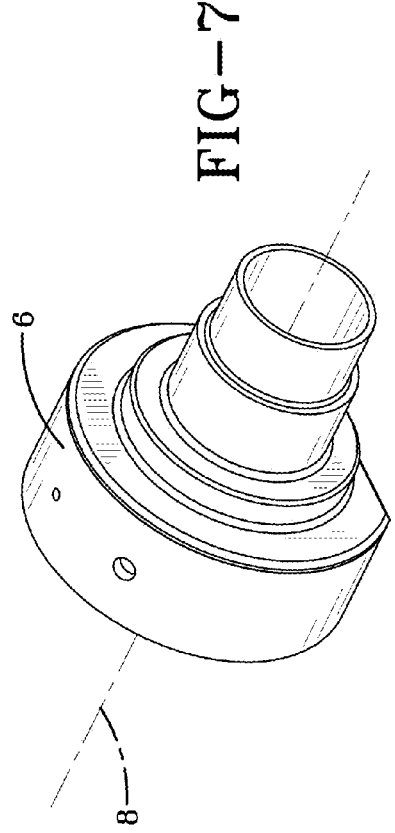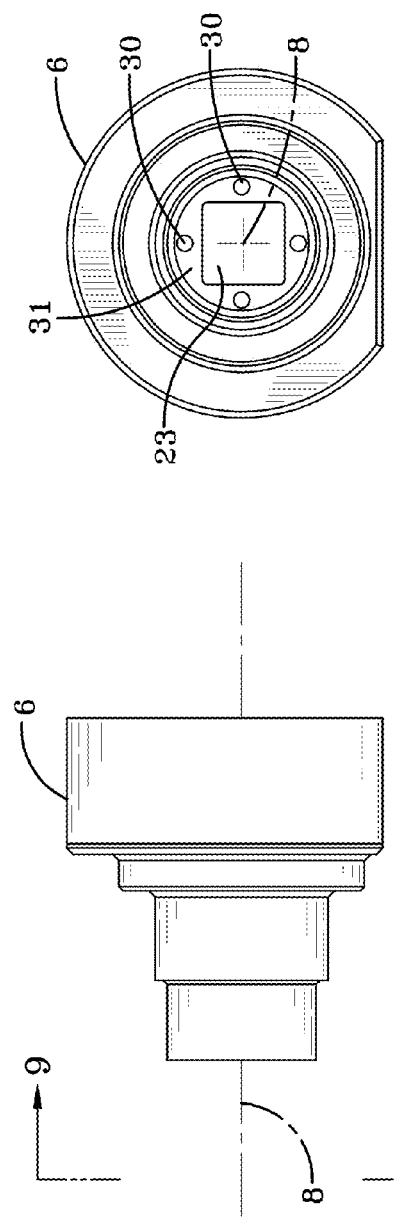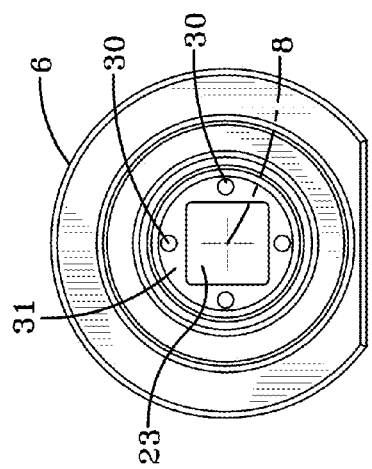

CONTROLLER

FIG-16 LED DRIVERS

BINOCULAR GLARE TESTING DEVICES

RELATED APPLICATION DATA

This application is a continuation of U.S. application Ser. No. 13/204,080, filed Aug. 5, 2011, now U.S. Pat. No. 8,690,332, which claims the priority benefit of U.S. Provisional Application Ser. No. 61/455,144, filed Oct. 15, 2010, which are hereby incorporated in their entirety herein by reference.

FIELD OF THE INVENTION

The field of the present invention generally relates to devices for testing eyes and, more particularly, to devices for assessing visual acuity in bright light conditions.

Cataracts are known to cause reduced vision and disabling glare. This is particularly significant for older patients driving an automobile at night. There is no accurate screening method currently available to measure vision in the presence of glare from headlights, streetlights and other bright sources of light in an otherwise dark environment. It is known that failure to treat patients with visually significant cataracts who may have difficulty driving at night increases the safety risk for themselves and others on the road. In addition, lack of adequate documentation of this visual impairment in patients with cataracts may result in denial for coverage of cataract surgery from Medicare and other insurance companies.

Glare testing devices are utilized to test a patient's visual acuity in conditions of bright light or glare. For examples of such devices see U.S. Pat. Nos. 4,784,483 and 6,783,239, the disclosures of which are expressly incorporated herein in their entireties by reference.

Although such glare testing devices have made this form of acuity testing relatively convenient and have encouraged such testing, currently available glare testers have less than desirable reproducibility of data.

Currently, there are no reliable and convenient methods to test for glare from oncoming headlights in patients with cataracts. Surgeons and other eye care providers may use a pen light to shine in the patient's eye as they ask the patient to read the standard Snellen chart. This test is very subjective as the light intensity and the angle of light to the eye is not constant and results vary from provider to provider.

In addition, current glare testers have not been made readily adaptable to use as or in binocular devices, such as manual refractors, automatic refractors (phoropters) and the like. These devices are designed for binocular vision testing and best simulate actual binocular vision for a patient and physician. Accordingly, there is a need in the art for improved glare testing devices, especially in the field of bilateral glare testing, such as in vision testing.

SUMMARY OF THE INVENTION

The present invention includes bilateral binocular glare testing devices, component portions thereof, and related methods of glare testing.

The invention is an improvement and variation upon the inventions disclosed in U.S. patent application Ser. No. 12/840,921, filed Jul. 21, 2010 and U.S. Provisional Application Ser. No. 61/227,561, filed Jul. 22, 2009, which are hereby incorporated in their entirety herein by reference.

Glare Tester with Plurality of Lights Around Sight Axis
Binocular Device with Eye Cups+Plurality of Lights Around Line of Sight Axis In general terms, the present invention includes a binocular glare tester attachment for use with a conventional or special purpose ophthalmic instrument, the binocular glare tester attachment comprising: a pair of eye cups, both the eye cups each comprising a wall partially enclosing a hollow interior chamber and having a viewing aperture defining a respective viewing line of sight axis for each eye cup, and a plurality of lights disposed around the line of sight axis.

Express Reference to Uniform Illumination

It is preferred that the plurality of lights is disposed around the line of sight axis so as to provide substantially uniform illumination about the line of sight axis.

Black Color

It is also preferred that at least the portion of each of the wall portions of said eye cup is non-reflective, preferably black.

Mounting Means where Ophthalmic Instrument is a Phoropter

The binocular glare tester attachment of the present invention typically and preferably will include mounting means for permanently or removably supporting the pair of eye cups on a phoropter. This may be any attachment means that is consistent with the comfortable and accurate operation of the device, such as tension clamps, screws, hand screws, screw clamps, permanent or releasable adhesives, magnets, etc.

With Interpupil Adjustment

The binocular glare tester attachment of the present invention will typically and preferably be attached to a phoropter or other vision testing device which has respective lenses each defining a respective lens line of sight axis. The mounting means attaches the pair of eye cups so as to align the viewing line of sight of the eye cups with the respective sight axis of the respective hollow interior chambers with the respective lens line of sight axis of the phoropter or other binocular vision testing device. In devices that are themselves capable of interpupil adjustment, the eye cups may be affixed and aligned so as to remain aligned with the respective lens line of sight axis of the phoropter or other vision testing device as it is adjusted.

In another embodiment, the binocular glare tester attachment may have its own adjustable support system, which may be in the form of any mechanical arrangement adapted to adjust and maintain the interpupil distance of the eye cup viewing lines. This may be in the form of binocular-type or opera-glass type supports, or in the form of a support bar supporting the pair of eye cups, at least one of the eye cups being moveably attached to the support bar so as to allow the distance between the pair of eye cups to be changed.

Where Plurality of Lights Provide Light within an Angle of Incidence Range

As to the angle of incidence, it is preferred that the plurality of lights are arrayed about the line sight axis so as to provide illumination such that within an angle of incidence of the light is limited to 10 to 25 degrees, most preferably 15 to 25 degrees, with respect to the location of the line of sight of the eye cup apertures.

Where Plurality of Lights are Two Different Wavelength Profiles

In order to be able to offer the advantage of different types of light, such as may be found in sunlight or various types of automobiles, the binocular glare tester attachment may feature a plurality of light sources that are adapted to provide illumination with light of two different wavelength profiles. This may be done through any means, such as through changes in the amount of current through the lights, the use of different filters, filaments or luminescent materials.

Using Two Different Types of Lights

It is most preferred that the binocular glare tester attachment of the present invention include a plurality of lights that comprise at least a first array adapted to provide illumination with light a first wavelength profile, and at least a second array adapted to provide illumination with light a second wavelength profile. It is most preferred that the two arrays are provided in an alternating fashion about an array circumference.

Where Plurality of Lights are in Alternating Arrays

It is also preferred that the first and second array of lights comprise a series of lights of different wavelength profiles placed in an alternating pattern around the line of sight axis.

Separate Switching

Where lights of different wavelength are used, it is preferred that the first array of lights and the second array of lights are provided with switches so as to be capable of being switched independently. This may be done for instance by use of any physical or electronic switching, and may be under microprocessor control.

Solid State LED Light and Boost Converter Variants

Current battery powered glare testers that use an incandescent lamp as the light source exhibit variations in wavelength and intensity as function of battery charge and lamp age. This variation will significantly affect the repeatability and reliability of testing conducted with glare testing devices.

Accordingly, it is preferred that the lights in the devices of the present invention utilize a combination of solid state white light LED light sources and electronic boost converters to maintain constant light intensity and wavelength independent of battery charge and instrument age. Different LED sources can be selected having wavelength characteristics that mimic various types of automobile headlights. For example, some headlights may have a spectral distribution with more blue than others. Selecting an LED that matches this spectral distribution along with one having a more standard spectral distribution allows glare from a range of headlight conditions to be tested. The solid state LED wavelengths are thus fixed by its inherent properties and the boost converter ensures a constant drive voltage to the LED ensuring constant light intensity. While the lights may use any AC or DC power source, it is preferred that the plurality of lights are solid state light emitting diodes electrically connected to a boost converter. This may be supplied in the form of any electronic circuitry adapted to provide the boost conversion, and may be under microprocessor control.

Binocular System with Shutters Variant

In order to allow the testing of individual eyes, the binocular glare tester attachment of the present invention optionally may include the means for shuttering each viewing aperture. It is most preferred that the means for shuttering the viewing apertures are adapted to shutter the viewing apertures optionally both separately or simultaneously.

The shutters may be of any type or geometry, although shutters of a camera-type shuttering geometry are preferred. The shutters may be actuated through any desired physical or electronic movements(s) which, as desired may be under microprocessor control.

Own On-Board Rechargeable Power Source

Where desired, the phoropter or other binocular vision testing device of the present invention may include an attachment that additionally comprises a rechargeable battery adapted to supply electric current to the plurality of lights. This power source may be used as the sole power source, or as a back-up power source for available AC power, provided with any electronic circuitry adapted to supply the current in accordance with the desired power arrangement.

Phoropter-Specific Claims: With Eye Cups+Plurality of Lights Around Line of Sight Axis+Interpupil Adjustment In a preferred embodiment, the present invention also includes a phoropter or other binocular vision testing device having a binocular glare tester portion or attachment, the binocular glare tester attachment comprising: a pair of eye cups, both the eye cups each comprising a wall partially enclosing a hollow interior chamber and having a viewing aperture defining a respective viewing line of sight axis, and a plurality of lights disposed around the line of sight axis, the pair of eye cups attached to the phoropter so as to allow adjustment of the distance between the pair of eye cups.

Mounting Means where Ophthalmic Instrument is a Phoropter

The binocular glare tester attachment or portion may be adapted to an existing phoropter or other binocular vision testing device, such as by additionally comprising mounting means for removably supporting the pair of eye cups on an existing phoropter or other binocular vision testing device, or may be integrated into the design of an original equipment device.

With Interpupil Adjustment

Typically, the phoropter has respective lenses each defining a respective lens line of sight axis, and the mounting means attaches the pair of eye cups so as to align the viewing line of sight axes of the respective hollow interior chambers with respective lens line of sight axes of the phoropter.

Where Plurality of Lights Provide Light within an Angle of Incidence Range

It is most preferred that the lights are arrayed about the sight line axis so as to provide illumination such that within an angle of incidence of the light is limited to 10 to 25 degrees, most preferably 10 to 25 degrees, in relation to the sight line axis.

Where Plurality of Lights are Two Different Wavelength Profiles

In order to be able to present glare representative of different environments, the binocular glare tester device preferably may feature a plurality of lights adapted to provide illumination with light of two different wavelength profiles. This feature may be provided in the form of lights adapted to have their wavelength profile varied through electronic means in accordance with known electronic theory and practice, or through the use of a plurality of lights that comprise a first array adapted to provide illumination with light a first wavelength profile, and a second array adapted to provide illumination with light a second wavelength profile. In such an embodiment, the first and second array of lights preferably will be in the form of a series of lights of different wavelength profiles placed in an alternating pattern around the line of sight axis. It is also preferred that the first array of lights and the second array of lights are provided with switches so as to be capable of being switched independently.

Other Embodiments

The present invention includes additional embodiments including those representing improvements over devices described in U.S. Pat. Nos. 4,784,483 and 6,783,239. The present invention includes embodiments wherein the device as disclosed in U.S. Pat. No. 6,783,239 may be rendered to a binocular version. This version likewise is an improvement and variation upon the inventions disclosed in U.S. patent application Ser. No. 12/840,921, filed Jul. 21, 2010 and U.S. Provisional Application Ser. No. 61/227,561, filed Jul. 22, 2009, which are hereby incorporated in their entirety herein by reference.

The present invention includes a binocular glare tester for use in ophthalmic test equipment other than solely as an attachment to a phoropter. The invention may be an attachment to or an integral part of a range of ophthalmic test equipment including but not limited to automatic and manual refractors.

The present invention includes a binocular glare tester attachment for use with a conventional hand-held ophthalmic instrument having a source of illumination, the binocular glare tester attachment comprising: a pair of eye cups or shells as described herein, eye cups or shells each comprising a wall partially enclosing a hollow interior chamber, each wall having respective light arrays; and mounting means for removably supporting the pair of eye cups or shells on the conventional hand-held ophthalmic instrument.

The binocular glare tester attachment may have any type of attachment means to allow the pair of eye cups or shells to be attached to any type of conventional hand-held ophthalmic instrument.

The binocular glare tester attachment of the present invention may use any mechanical or other means for changing the distance between the pair of eye cups or shells, such as, for instance, a support rod affixed to one of the eye cups or shells, a bracket slidingly engaging the support rod, and the other of the eye cups or shells affixed to the bracket; and means for directing the illumination from the interior surface of each cup or shell along the respective visual axis thereof.

The source of illumination may be adapted to provide illumination with light of two different wavelength profiles, such as by using the electronic means described herein for the provision of light of different wavelength profiles.

The glare tester may have a source of illumination comprising solid state light emitting diodes and a booster converter, the light emitting diodes typically disposed on or in the facing wall partially enclosing a hollow interior chamber.

The present invention further includes a conventional hand-held ophthalmic instrument bearing the binocular glare tester attachment of the present invention, and such conventional hand-held ophthalmic instrument for instance may be an ophthalmic transilluminator or an ophthalmoscope.

The present invention also includes methods of glare testing, such as may be carried out through use of the devices of the present invention, in accordance with and adapting vision testing techniques and practices to the use of the present invention. The method comprises the steps of having the patient peer through the sight apertures while the device is used to provide simulative glare. The type and amount of glare may be varied as may be the size of the sight aperture(s) and whether one or both eyes are assayed. The wavelength can be varied discretely or additively through the use of optional light source arrays as described. Shuttering of any form may be used to allow the visual acuity of a patient's eye to be tested independently, such as sequentially or comparatively.

For instance, the method of testing a patient with respect to visual acuity under the influence of light, typically will comprise the steps: (1) positioning a patient in the vision-testing position of a phoropter, the phoropter being provided with a binocular glare tester attachment for use with a conventional ophthalmic instrument, the binocular glare tester attachment comprising: a pair of eye cups, both the eye cups each comprising a wall partially enclosing a hollow interior chamber and having a viewing aperture defining a respective viewing line of sight axis for each eye cup, and a plurality of lights disposed around the line of sight axis; (2) presenting the patient with a visual acuity chart or pattern; (3) conducting a visual acuity test of the patient by assessing the patient's ability to visually perceive the visual acuity chart or pattern while the patient's vision is under the influence of the plurality of lights.

In a preferred embodiment, the phoropter comprises a shutter mechanism governing each sight axis, and wherein the method includes the step of alternatively shuttering each sight axis during the visual acuity test so as to test the visual acuity of the patient's eye independently.

BRIEF DESCRIPTION OF THE DRAWINGS

These and further features of the present invention will be apparent with reference to the following description and drawings, wherein:

FIG. 1C is a detailed front elevation photographic view of a portion of a binocular glare testing device in an active position as applied to a phoropter, in accordance with one embodiment of the present invention.

FIG. 7 is a detailed side perspective view of an eye shell of a binocular glare testing device for attachment to a phoropter, in accordance with one embodiment of the present invention.

FIG. 8 is a detailed side elevation view of an eye shell of a binocular glare testing device for attachment to a phoropter, in accordance with one embodiment of the present invention.

FIG. 9 is a detailed rear elevation view of an eye shell of a binocular glare testing device for attachment to a phoropter, in accordance with one embodiment of the present invention.

Figure 1:
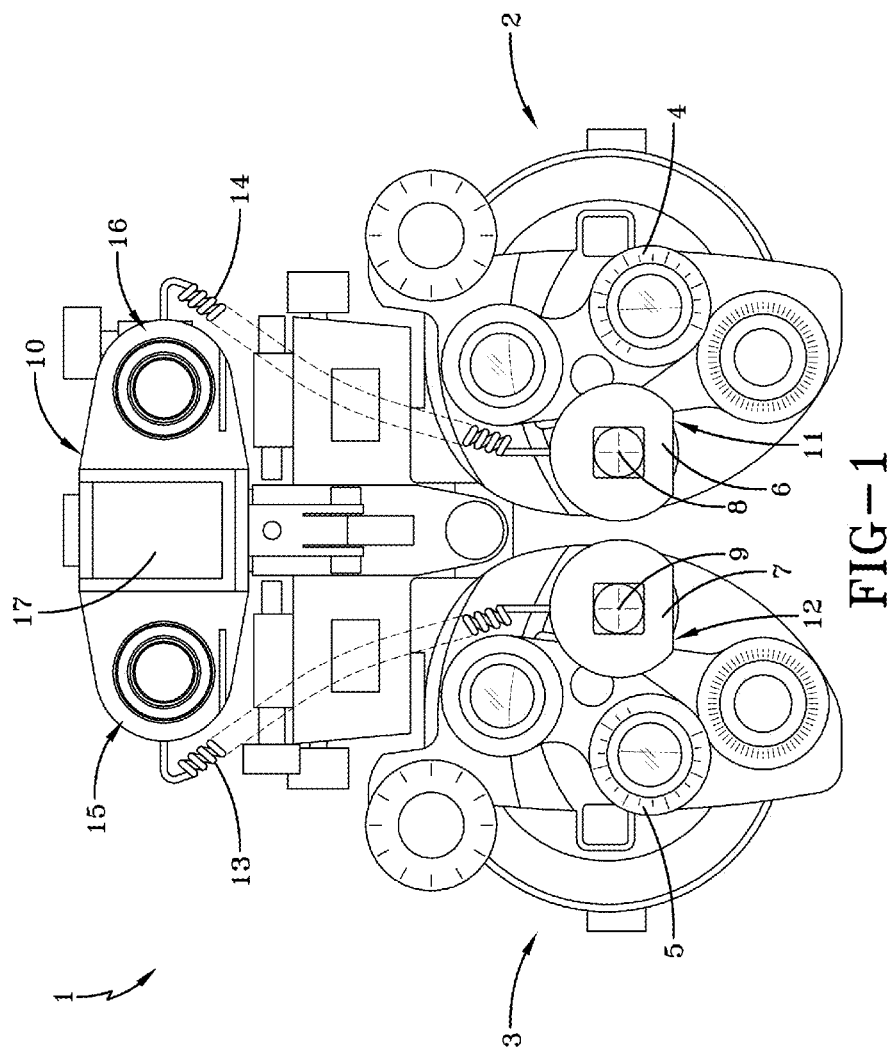
FIG. 1 is a front elevation photographic view of a binocular glare testing device in an active position as applied to a phoropter, in accordance with one embodiment of the present invention.

It should be understood that the appended drawings are not necessarily to scale, presenting a somewhat simplified representation of various preferred features illustrative of the basic principles of the invention. The specific design features of binocular glare testing devices as disclosed herein, including, for example, specific dimensions, orientations, locations and shapes will be determined in part by the particular intended application and use environment. Certain features of the illustrated embodiments have been enlarged or distorted relative to others to facilitate visualization and clear understanding. In particular, thin features may be thickened, for example, for clarity or illustration. All references to direction and position, unless otherwise indicated, refer to the orientation of the binocular glare testing devices illustrated in the drawings.

DETAILED DESCRIPTION OF CERTAIN PREFERRED EMBODIMENTS

In light of the foregoing summary, the following presents a detailed description of the preferred embodiments of the present invention which are considered to be the best mode thereof.

It will be apparent to those skilled in the art that is, to those who have knowledge or experience in this area of technology, that many uses and design variations are possible for the improved binocular glare testing devices disclosed herein. The following detailed discussion of various alternative and preferred embodiments will illustrate the general principles of the invention with reference to preferred embodiments. Other embodiments suitable for other applications will be apparent to those skilled in the art given the benefit of this disclosure. Such other embodiments may be rendered, for instance, by combining characteristics and features of one embodiment with that of another, which may be done in any number of variations not inconsistent with the desired function or application.

Figure 2:
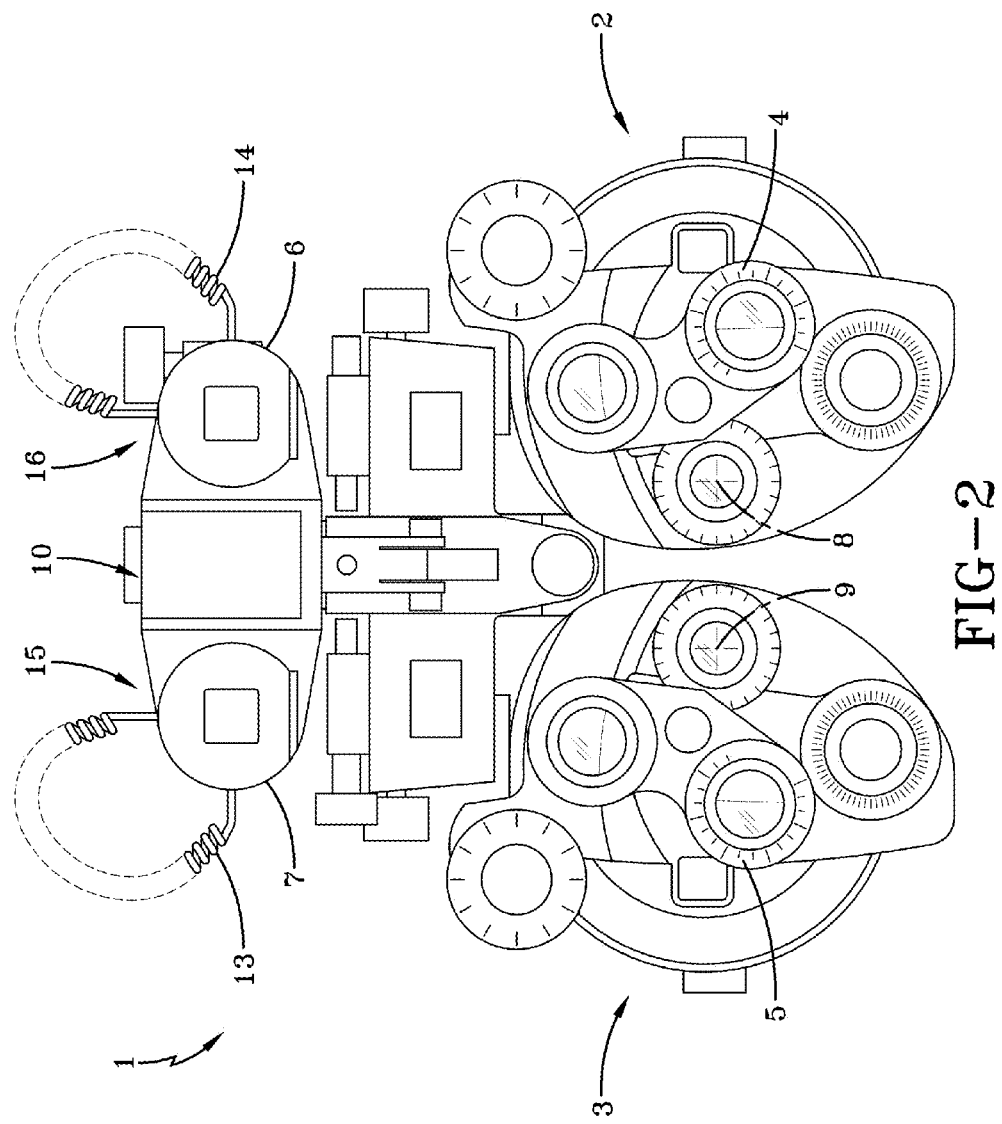
FIG. 2 is a front perspective photographic view of a binocular glare testing device in a stored position as applied to a phoropter, in accordance with one embodiment of the present invention.

Referring now to the drawings, FIGS. 1 and 2 illustrate a binocular glare testing device according to the present invention, as applied to or incorporated into a phoropter. The present invention may be adapted for use with any similar binocular testing device, such as those described in U.S. Pat. Nos. 7,562,982; 7,549,750; 7,533,993; 7,264,354; 6,056,402; 5,812,241; 5,648,833; 5,440,357; 5,420,651; 5,223,864; 4,861,156; and 4,385,813; and in U.S. Published Patent Applications Nos. 20080143960; 20080123054; 20070242224; 20070052924; 20060050238; 20040156021, all of which are hereby incorporated herein by reference.

The present invention may also be adapted from known glare testing devices, such as those described in U.S. Pat. No. 5,671,039, hereby incorporated herein by reference.

FIG. 1 is a front perspective view of a portion of a binocular glare testing device in an active position as applied to a phoropter, in accordance with one embodiment of the present invention. FIG. 2 is a front perspective view of a portion of a binocular glare testing device in a stored position as applied to a phoropter, in accordance with one embodiment of the present invention.

FIG. 1 shows a phoropter 1 having a binocular glare testing attachment in accordance with one embodiment of the present invention. The phoropter 1 has two sides 2 and 3 each with its own lens sets 4 and 5, respectively, used for refraction of the eye during sight testing, to measure an individual's refractive error and determine his or her eyeglass prescription. The two sides typically are adjustable with respect to one another so as to be capable of adjusting the active interpupil distance for the patient.

FIG. 1 also shows the eye cups or shells 6 and 7 of the glare tester attachment 10 which are respectively associated with the active sight apertures (not shown, but disposed respectively behind the eye cups or shells 6 and 7, as may be appreciated from FIG. 2) having respective active sight axes 8 and 9. The eye cups or shells 6 and 7 may be attached or supported in any way so as to align them with the active sight axes 8 and 9, and preferably may be attached to the respective sides 2 and 3 of the phoropter 1 by any appropriate means if provided as an after-market attachment. Accordingly, the binocular glare tester attachment typically and preferably will include mounting means for permanently or removably supporting the pair of eye cups on a phoropter. This may be any attachment means that is consistent with the comfortable and accurate operation of the device, such as tension clamps, screws, hand screws, screw clamps, permanent or releasable adhesives, magnets, etc.

The eye cups or shells 6 and 7 typically and preferably will be releasably attached through a mechanical arrangement that will allow their repetitive and reliably accurate alignment with the active sight axes 8 and 9, such as through the use of hand screws, slot-and-groove or pin-and-hole arrangements and/or magnetic attachments. Otherwise, the eye cups or shells 6 and 7 may be incorporated directly into the original phoropter construction in accordance with those construction techniques known in the field. Accordingly, these views show a pair of eye cups, both the eye cups each comprising a wall partially enclosing a hollow interior chamber and having a viewing aperture defining a respective viewing line of sight axis for each eye cup, a portion of each wall being provided with a plurality of lights disposed around the line of sight axis, as described herein.

As may be appreciated from FIGS. 1 and 2 as an example, the binocular glare tester attachment will typically and preferably be attached to a phoropter or other vision testing device which has respective lenses each defining a respective lens line of sight axis. The mounting means attaches the pair of eye cups so as to align the viewing line of the sight of the eye cups with the respective sight axis of the respective hollow interior chambers with the respective lens line of sight axis of the phoropter or other binocular vision testing device. In devices that are themselves capable of interpupil adjustment, such as shown in FIGS. 1 and 2, the eye cups may be affixed and aligned so as to remain aligned with the respective lens line of sight axis of the phoropter or other vision testing device as it is adjusted.

The binocular glare testing device includes a cup or shell with an open end and a closed end except for an aperture along a visual axis of each cup or shell. The cup or shell is designed to provide a substantially isolated light box about the space just beyond the lens placed in the active position (i.e., aligned with the active sight axes 8 and 9). As can be appreciated from FIG. 1, the eye cups or shells 6 and 7 may be placed into the active sight positions, 11 and 12 respectively, where the lens sets 4 and 5 otherwise would operate to provide the active sight positions (i.e., in alignment with the active sight axes 8 and 9) with lens sets of varying refraction for sight testing, while keeping the space just beyond the lens placed in the active position simultaneously free of extraneous light.

FIG. 1 also shows the glare tester attachment 10 which may contain a rechargeable battery pack to supply electric current to the light sources in the eye cups or shells 6 and 7 via respective electric conduits 13 and 14. The electric current to the light sources may be provided by a battery pack 17 governed by an electric switch. Alternatively, the light sources in the eye cups or shells may be supplied with direct line current from a source in the examination suite.

The eye cups or shells 6 and 7 preferably may be provided with status indicator lights, such as in light arrays 18 and 19, that may be used to indicate to the user, for instance, whether the lights within each eye cup or shell are illuminated, whether there is a low battery condition, and, in cases where arrays of lights of different wavelength profiles are being used, which arrays are being illuminated.

Also shown in FIG. 1 are the storage receptacles 15 and 16 for holding, respectively, eye cups or shells 6 and 7, as shown in FIG. 2. This allows the phoropter 1 to be used normally without interference from the glare tester attachment 10 and its eye cups or shells 6 and 7.

In each of eye cups or shells 6 and 7, a light source provides a ring of light about each sight aperture. The ring of light is provided near the aperture and preferably contiguous with the aperture so that the light source is close to the visual axis. The illustrated light source is a ring of LEDs located within the shell about the aperture. It is noted however, that the light source can be of any suitable type and the light source can have any suitable configuration which provides a ring of light about the aperture and visual axis.

It is most preferred that the lights contained in eye cups or shells 6 and 7 are arrayed about the sight line axis so as to provide illumination such that within an angle of incidence of the light is limited to 10 to 25 degrees, most preferably 10 to 25 degrees, in relation to the sight line axis. It is further preferred that the binocular glare tester devices feature a plurality of lights adapted to provide illumination with light of two different wavelength profiles. This feature may be provided in the form of lights adapted to have their wavelength profile varied through electronic means in accordance with known electronic theory and practice, or through the use of a plurality of lights that comprise a first array adapted to provide illumination with light a first wavelength profile, and a second array adapted to provide illumination with light a second wavelength profile. In such an embodiment, the first and second array of lights preferably will be in the form of a series of lights of different wavelength profiles placed in an alternating pattern around the line of sight axis. It is also preferred that the first array of lights and the second array of lights are provided with switches so as to be capable of being switched independently. Each array of lights likewise may be controlled through any effective equivalent electrical means, such as through on-board integrated circuits and relays to be able to activate each array independently.

In a preferred embodiment, the binocular glare testing device according to the present invention may feature sight apertures that may be individually shuttered and/or adjustable. That is, the size of each aperture may be manually changed to a desired size. The illustrated aperture in eye cups or shells 6 and 7 may be constructed similarly to a camera aperture but it is noted that any suitable type of adjustable aperture can be utilized. For example, an adjustable aperture is available from the Merit Corporation of Schenectady, N.Y., which has a shutter type aperture which is adjusted by rotating an outer thumb wheel that may be adapted to the construction of this embodiment. As an alternative, the phoropter may be provided with a similar shuttering mechanism to reduce the size of the effective sight aperture.

Figure 1B:
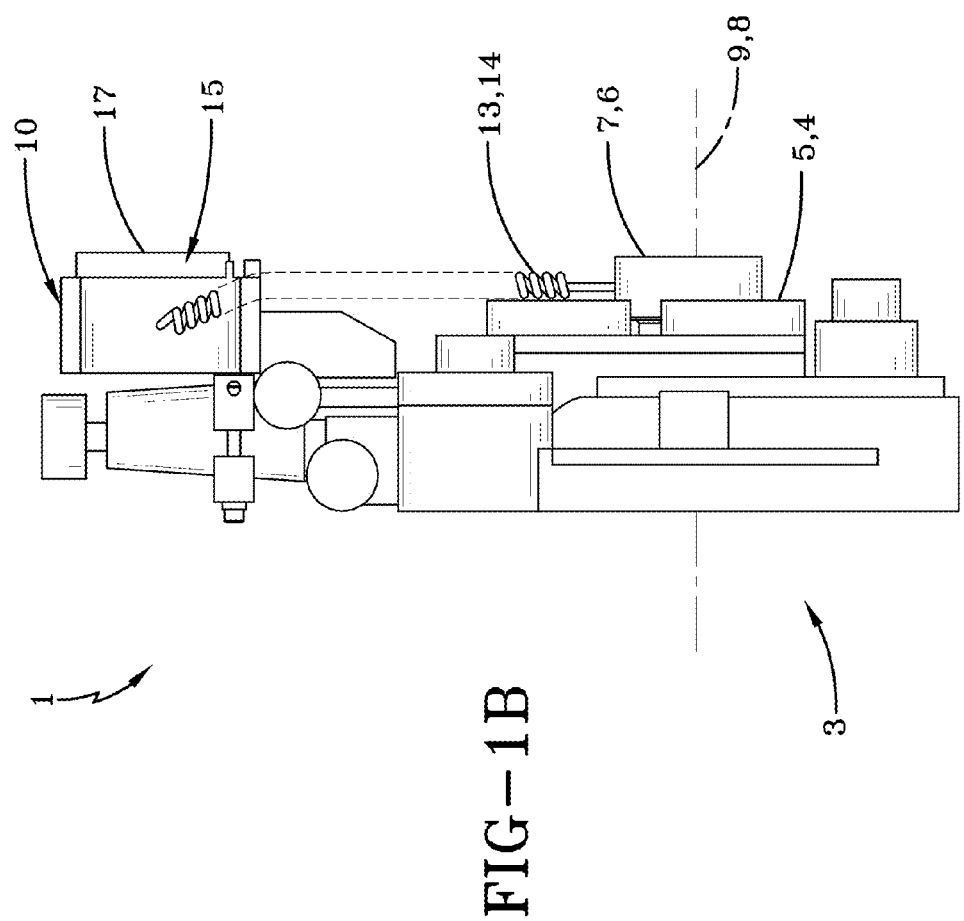
FIG. 1B is a side elevation photographic view of a binocular glare testing device in an active position as applied to a phoropter, in accordance with one embodiment of the present invention.

FIG. 1B is a side elevation photographic view of a binocular glare testing device in an active position as applied to a phoropter, in accordance with one embodiment of the present invention, and in which like reference numerals refer to the same portions as in FIG. 1.

FIG. 1C is a detailed front elevation photographic view of a portion of a binocular glare testing device in an active position as applied to a phoropter, in accordance with one embodiment of the present invention, and in which like reference numerals refer to the same portions as in FIG. 1. This view shows a human eye 9a of a user peering along active sight axis 9 of eye cup or shell 7, as shown in FIG. 1, and bathed in glare light as can be appreciated from the operation of the device.

Figure 1D:
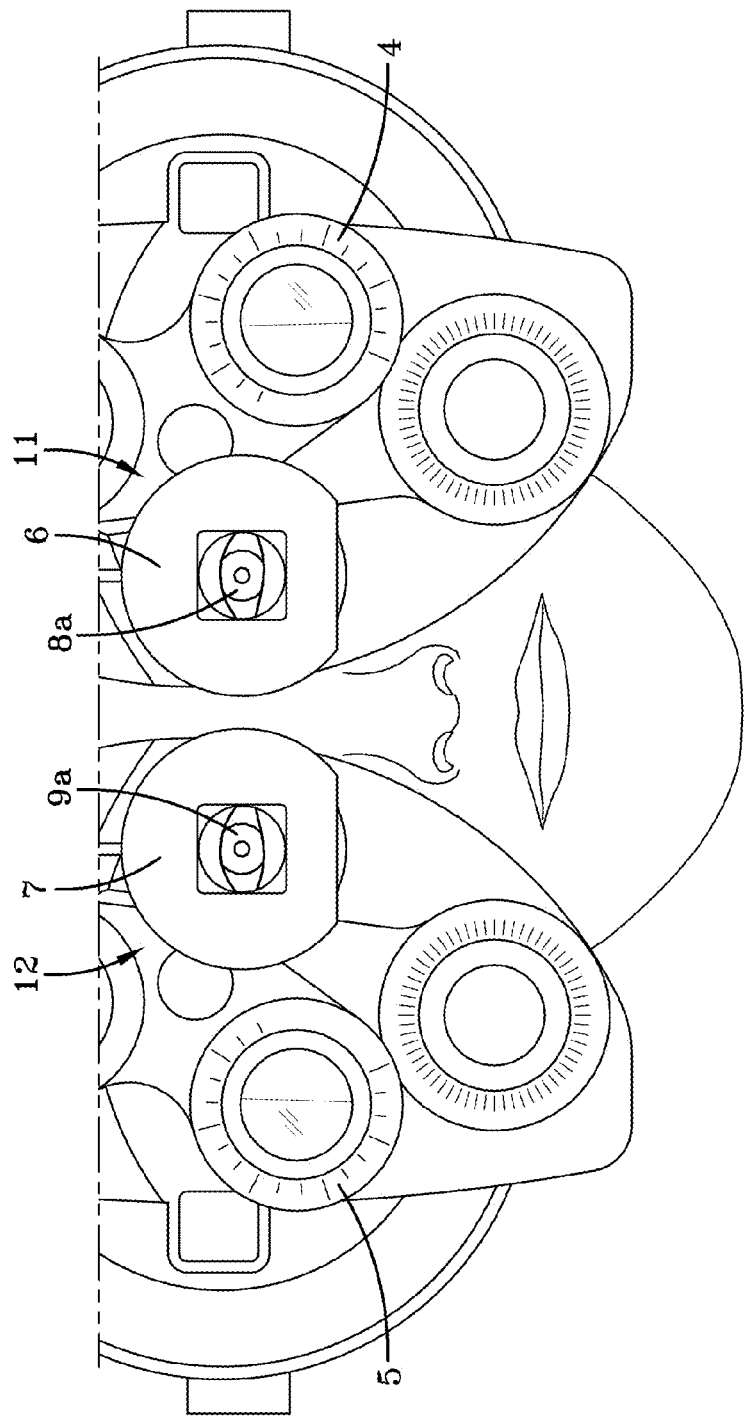
FIG. 1D is a detailed front elevation photographic view of a portion of a binocular glare testing device in an active position as applied to a phoropter, in accordance with one embodiment of the present invention.

FIG. 1D is a detailed front elevation photographic view of a portion of a binocular glare testing device in an active position as applied to a phoropter, in accordance with one embodiment of the present invention, and in which like reference numerals refer to the same portions as in FIG. 1. This view shows human eyes 8a and 9a of a user peering along active sight axes 9 and 8, respectively of eye cups or shells 7 and 6, respectively, as shown in FIG. 1, and bathed in glare light as can be appreciated from the operation of the device.

FIG. 2 is a front perspective view of a portion of a binocular glare testing device with the eye cups or shells in a stored position as applied to a phoropter, in accordance with one embodiment of the present invention, and using like reference numerals to those used with respect to FIG. 1. This view shows how the eye cups or shells 7 and 6 are stored in storage receptacles 15 and 16 of glare tester attachment 10.

Figure 2B:
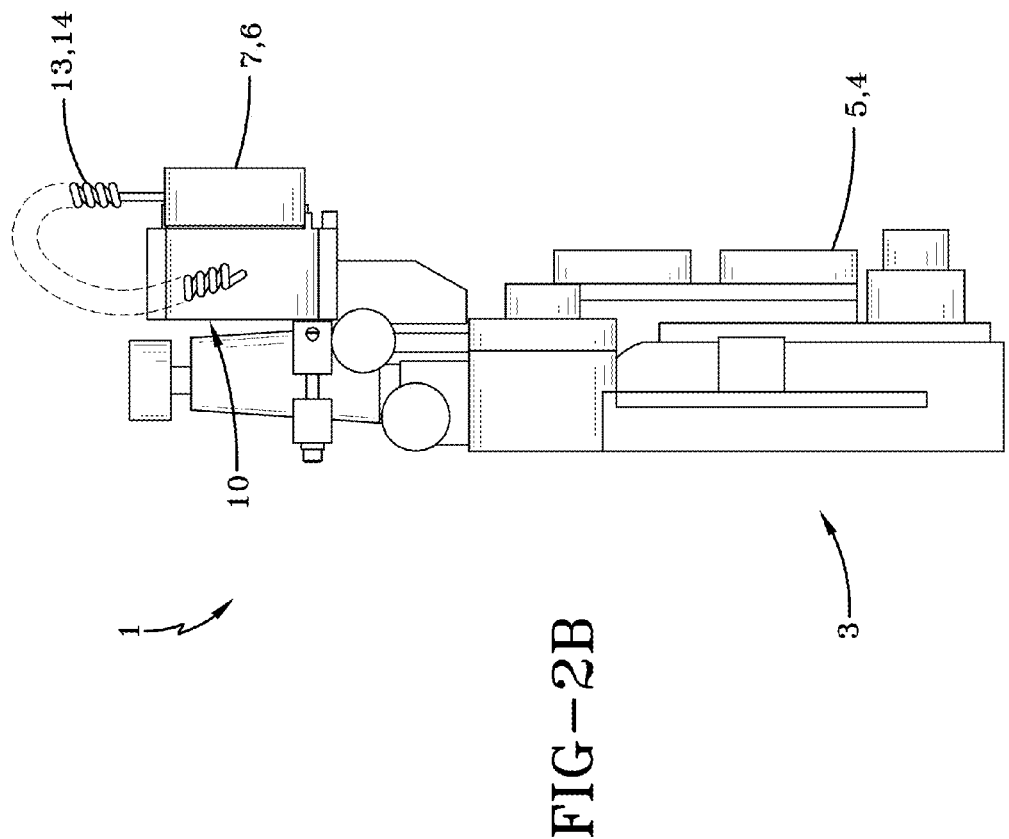
FIG. 2B is a side elevation photographic view of a binocular glare testing device in a stored position as applied to a phoropter, in accordance with one embodiment of the present invention.

FIG. 2B is a side perspective view of a portion of a binocular glare testing device with the eye cups or shells in a stored position as applied to a phoropter, in accordance with one embodiment of the present invention, and using like reference numerals to those used with respect to FIG. 1. This view shows how the eye cups or shells 7 and 6 are stored in storage receptacles 15 and 16 of glare tester attachment 10.

Figure 3:
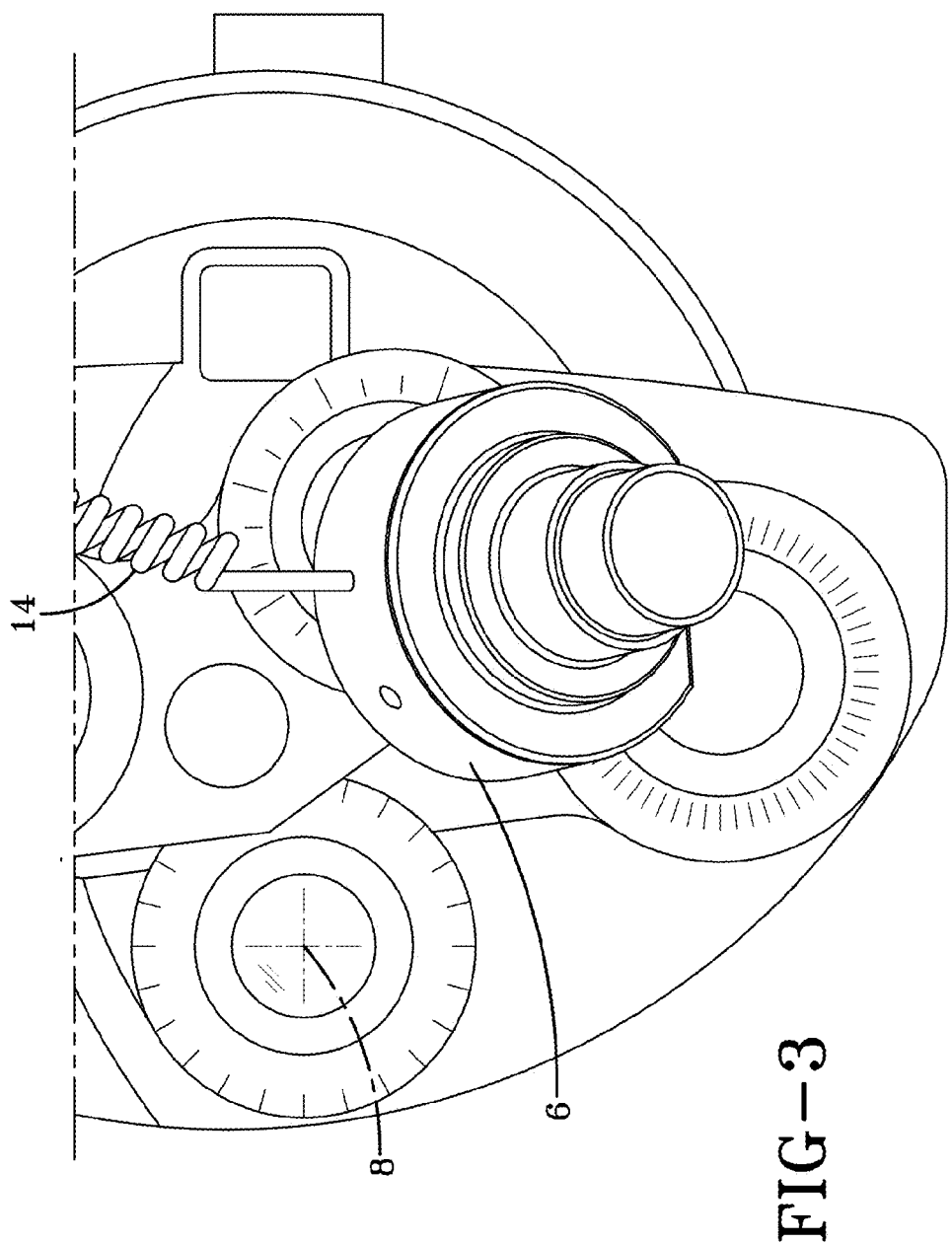
FIG. 3 is a detailed perspective photographic view of a portion of a binocular glare testing device in a disassembled position on a phoropter, in accordance with one embodiment of the present invention.

FIG. 3 is a detailed photographic view of a portion of eye cup or shell 6, as shown in FIG. 1, taken from its operative position in the active position along active sight axis 8, and inverted to show the shape of the eye cup or shell 6 that extends into the aperture of the phoropter defining sight axis 8. As can be appreciated from FIG. 3, the eye cups or shells 6 and 7 may be removed from their position partially extending into the active sight apertures of the phoropter to permit the lens sets 4 and 5 to operate to provide the active sight positions (i.e., in alignment with the active sight axes 8 and 9) with lens sets of varying refraction for sight testing, while keeping the space just beyond the lens placed in the active position simultaneously free of extraneous light. The eye cups or shells 6 and 7 may be stored as shown in FIG. 2 when not in use. When placed in the active sight apertures of the phoropter, the eye cups or shells 6 and 7 preferably may be sized such that they extend within the phoropter body to be secured in place, but may allow actuation of the phoropter shutter system, to allow independent glare testing of either eye.

Figure 4:
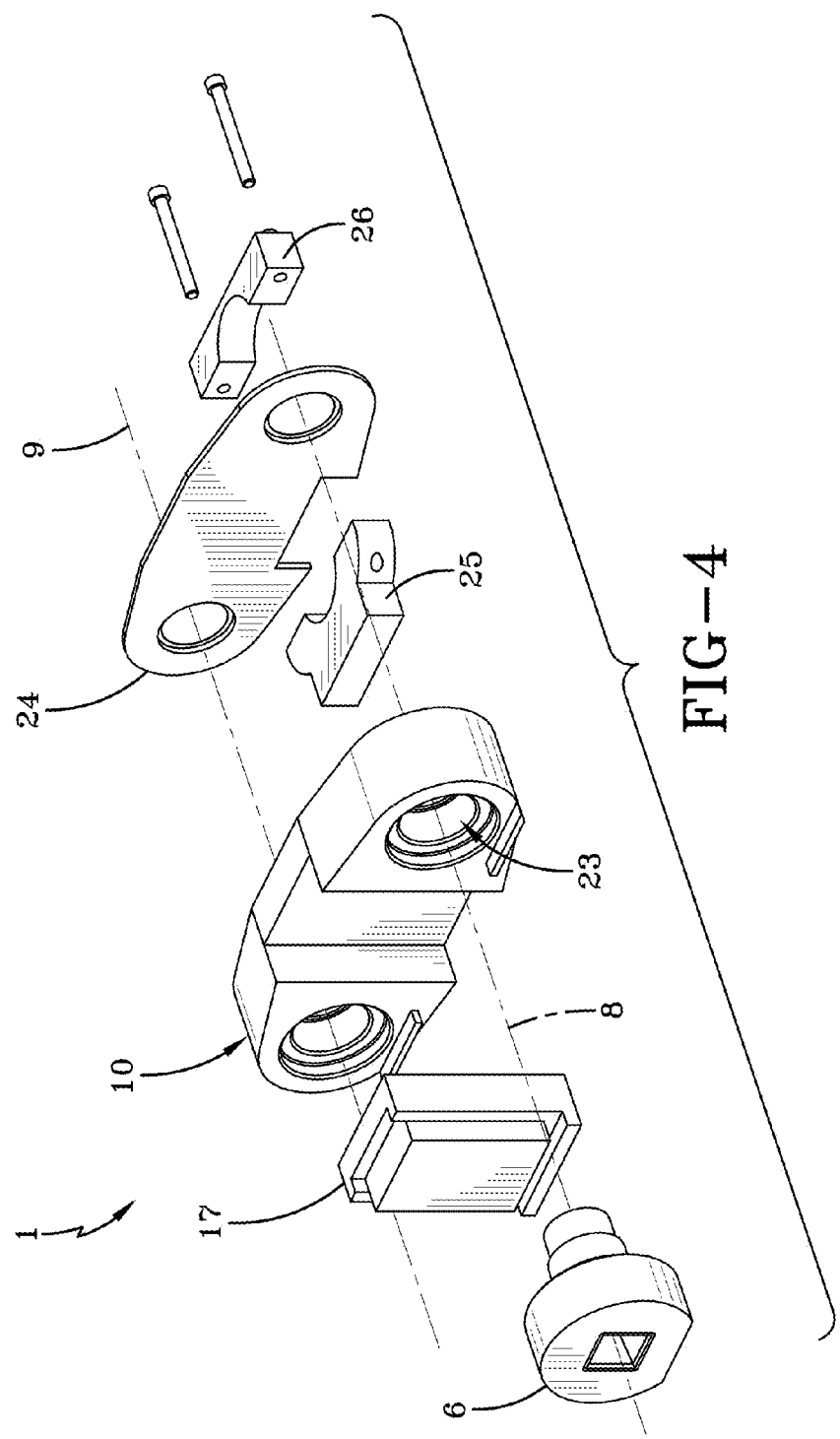
FIG. 4 is an exploded frontal perspective view of a portion of a binocular glare testing device as may be applied to a phoropter, in accordance with one embodiment of the present invention.
Figure 5:
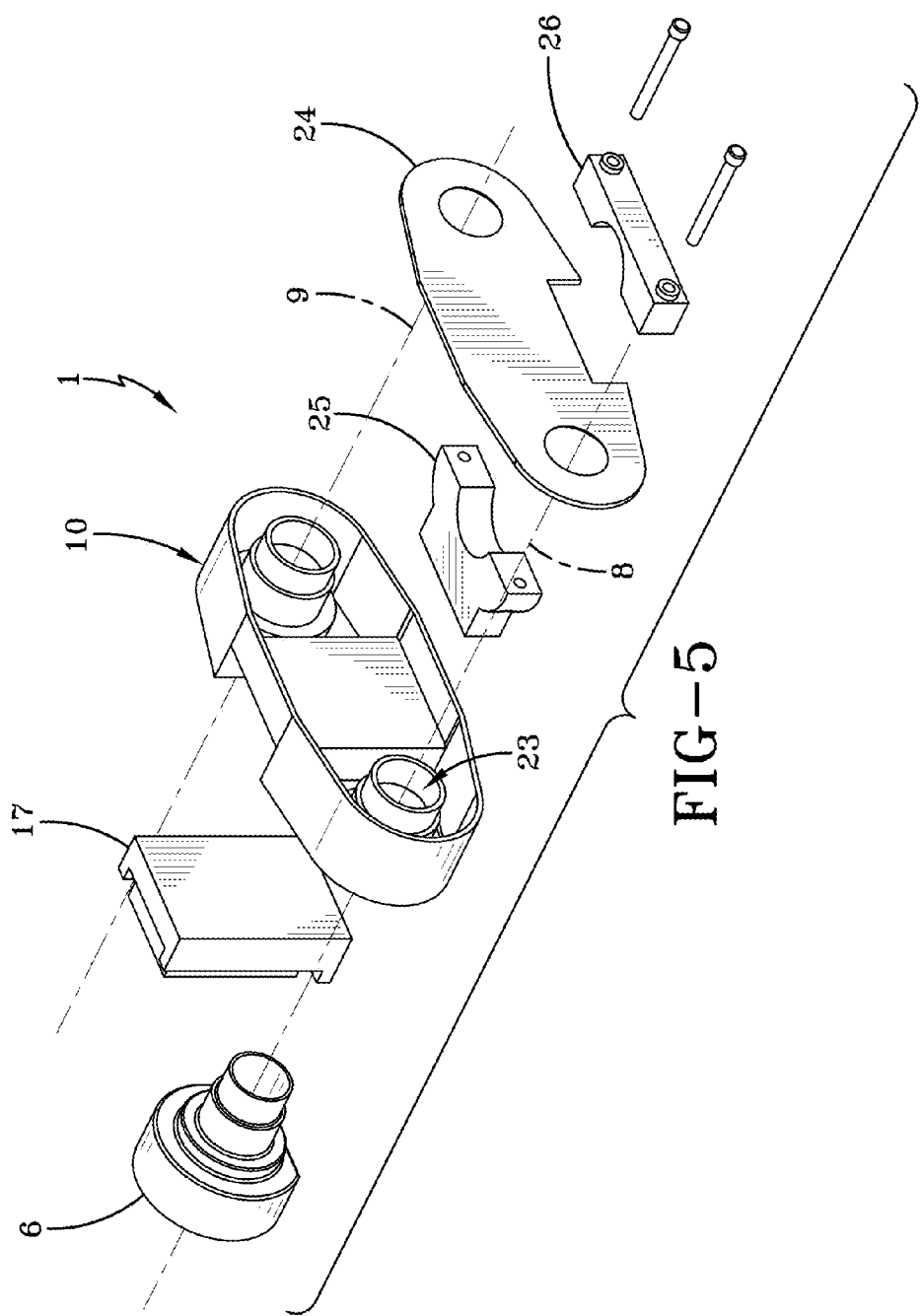
FIG. 5 is an exploded rear perspective view of a portion of a binocular glare testing device as may be applied to a phoropter, in accordance with one embodiment of the present invention.

FIGS. 4 and 5 are exploded views of a portion of the binocular glare testing device 1, as applied to a phoropter, in accordance with one embodiment of the present invention as applied to a phoropter, and wherein the reference numerals used in the foregoing Figures are used where applicable.

FIG. 4 shows an exploded front perspective view of a glare tester attachment 10 which may contain a rechargeable battery pack to supply electric current to the light sources in the eye cups or shell, such as eye shell 6, or otherwise be supplied with DC or line current to the light sources in the eye cups or shells, via respective electric conduits, not shown. The electric current to the light sources may be governed by an electric switch disposed at any operationally convenient surface of the glare tester attachment 10. Alternatively, the light sources in the eye cups or shells may be supplied with direct line current from a source in the examination suite.

FIG. 4 also shows main body portion 10 having apertures such as 23 into which eye shell 6 may fit by virtue of its corresponding releasable shape such as shown, and may be attached through any appropriate permanent or releasable attachment, such as through a set screw, interference fit, magnetic fitting etc. The eye shell 6 may be releasably attached so as to be removable for cleaning or replacement.

FIG. 4 also shows the eye cups or shells of the glare tester attachment 10 which are respectively associated with the active sight apertures of a phoropter (not shown, but disposed respectively behind the main body portion 10 and eye shell 6 and its correspondent on the left side (not shown), as also may be appreciated from FIG. 5), and having respective active sight axes 8 and 9. The eye cups or shells, such as shell 6, may be attached or supported in any way so as to align them with the active sight axes 8 and 9, and preferably may be attached to the phoropter by any appropriate means if provided as an after-market attachment. The eye cups or shells, such as eye shell 6, typically and preferably will be releasably attached through a mechanical arrangement that will allow their repetitive and reliably accurate alignment with the active sight axes 8 and 9, such as though the use of hand screws, slot-and-groove or pin-and-hole arrangements and/or magnetic attachments. Otherwise, the eye cups or shells may be incorporated directly into the original phoropter construction in accordance with those construction techniques known in the field.

FIG. 4 also shows an optional back plate 24 which may be used to attach the main body 10 to the phoropter, by its attachment thereto, such as through fitting holes shown in this view permitting screw attachment to the main body portion 10; and such as by cooperative interaction of releasable clamp portions 25 and 26. Clamp portions 25 and 26 may be sized and shaped to cooperate with any convenient and effective supportive portion of the associated phoropter, such as by engaging a vertical cylindrical portion as suggested by the shape of the opposed clamp portions 25 and 26, which may also be affixed by screws as suggested by the pocket holes provided therein. This is shown for example in FIG. 6.

FIG. 5 is an exploded rear perspective view of a portion of a binocular glare testing device 1 as applied to a phoropter, in accordance with another embodiment of the present invention as shown in FIG. 4, and using like reference numerals to those used with respect to FIG. 4.

As may be appreciated from FIGS. 4 and 5, in other embodiments of the invention, the binocular glare tester attachment may have its own adjustable support system, which may be in the form of any mechanical arrangement adapted to adjust and maintain the interpupil distance of the eyecup viewing lines. For instance, main body portion 10 may be rendered in two or more sub-portions (such as in the nature of a binocular-type mechanical arrangement), each bearing an eye shell, such as eye shell 6, and that may be adapted to move with respect to one another so as to permit the eye shells to be repositioned effectively to move the active sight axes 8 and 9 closer or further from one another, and to be able to be aligned with the sight axes of the presented active phoropter lenses.

Figure 6:
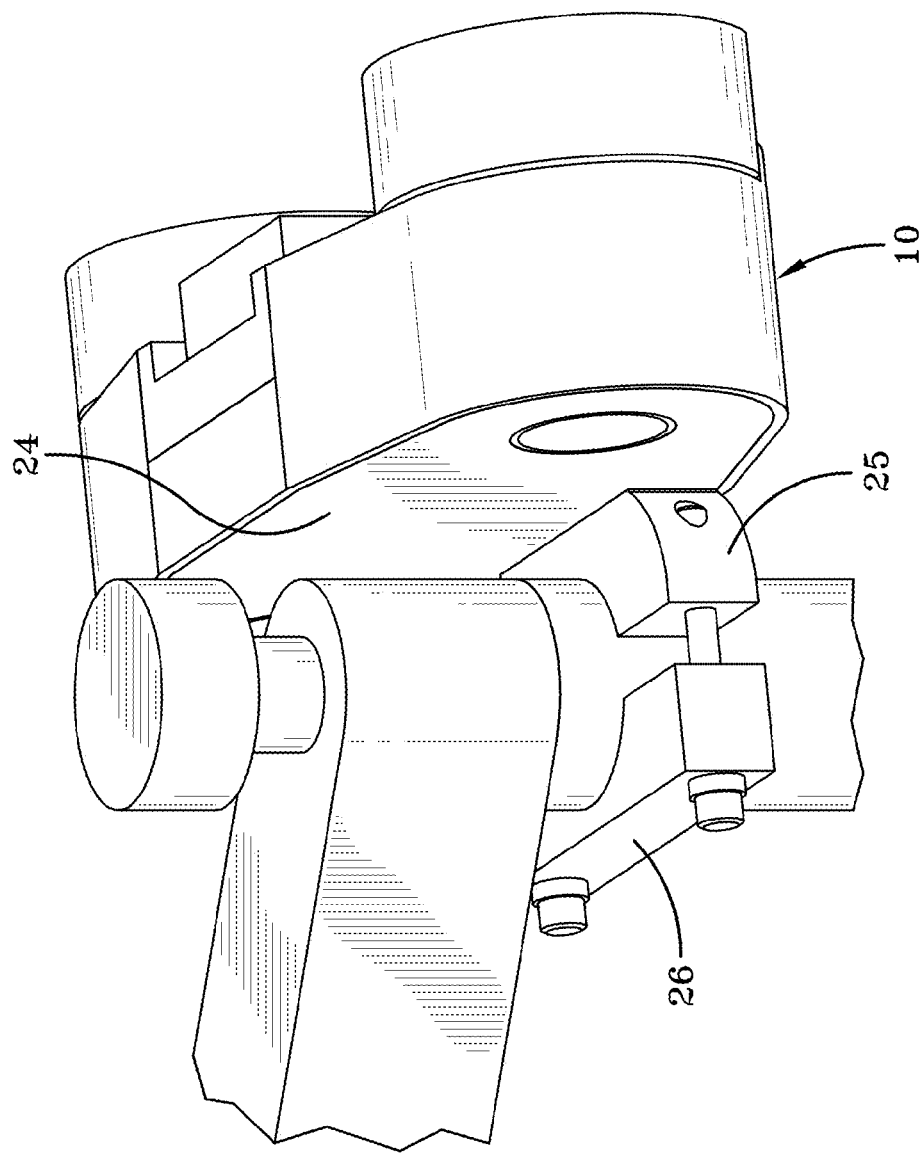
FIG. 6 is a detailed perspective photographic view of a portion of a binocular glare testing device attached to a phoropter, in accordance with one embodiment of the present invention.

FIG. 6 is a detailed perspective photographic view of a portion of a binocular glare testing device attached to a phoropter, in accordance with one embodiment of the present invention, and using like reference numerals to those used with respect to FIGS. 4 and 5.

FIG. 7 is a detailed side perspective view of an eye shell or cup 6 of a binocular glare testing device for attachment to a phoropter, in accordance with one embodiment of the present invention, and using like reference numerals to those used with respect to FIGS. 4 and 5. This Figure shows the shaping of the eye shell or cup 6 that allows it to be fit into the corresponding structure of the phoropter, as may be appreciated from FIG. 3.

FIG. 8 is a detailed side elevation view of an eye shell of a binocular glare testing device for attachment to a phoropter, in accordance with one embodiment of the present invention, and using like reference numerals to those used with respect to FIGS. 4 and 5.

FIG. 9 is a detailed rear elevation view of an eye shell of a binocular glare testing device for attachment to a phoropter, and using like reference numerals to those used with respect to FIGS. 4 and 5. FIG. 9 is a detailed front elevation view of an eye shell 6 of a binocular glare testing device 1 for attachment to a phoropter, shown in FIGS. 4 and 5. This view shows the array of light emitting diodes 30 disposed along the facing wall 31, which includes the framed aperture 23 centered about active sight axis 8. It is preferred that the plurality of lights are disposed around the line of sight axis so as to provide substantially uniform illumination about the line of sight axis, and that at least the portion of each of the wall portions being provided with the plurality of lights is non-reflective, preferably black.

Figures 10, 11:
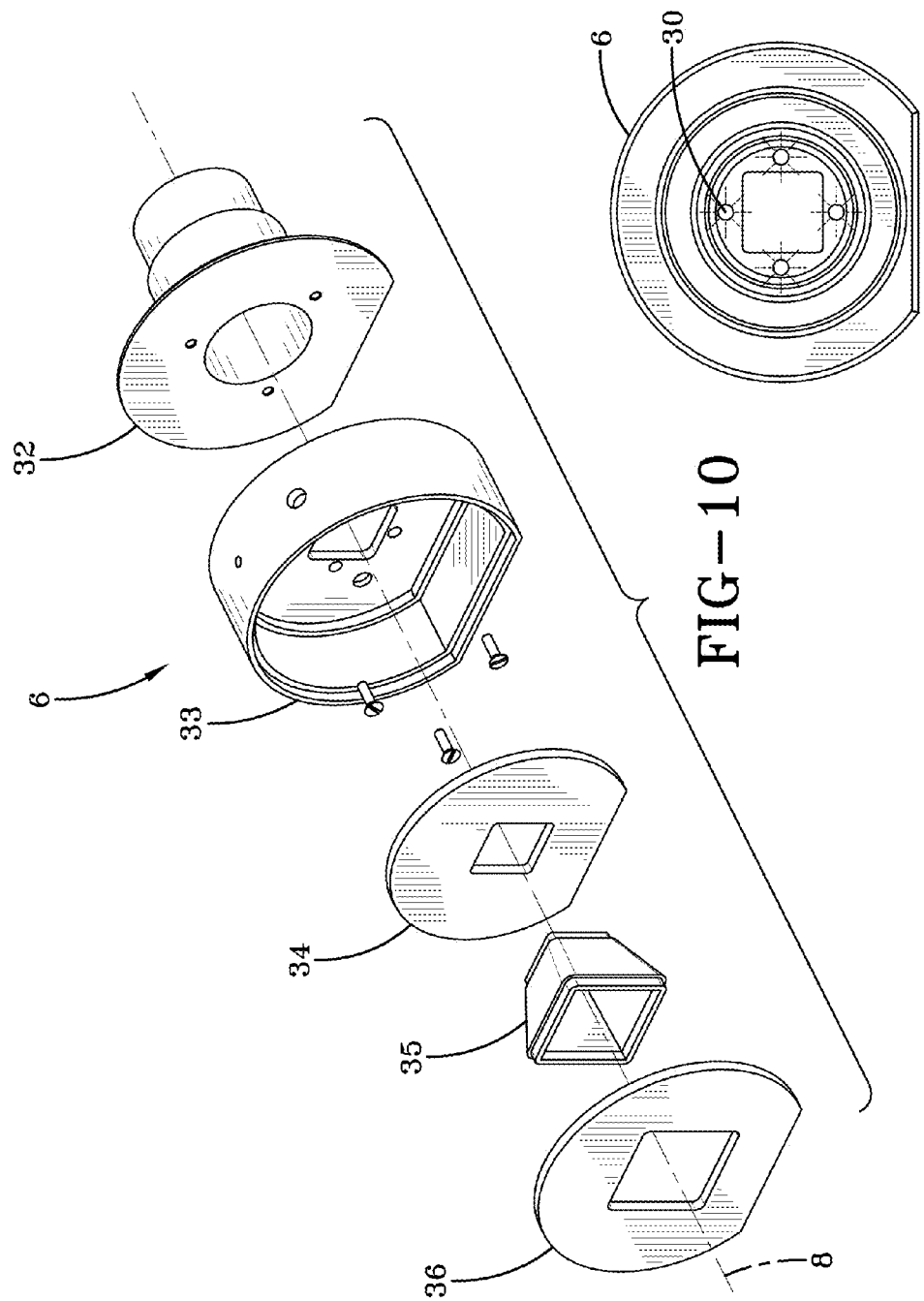
FIG. 10 is an exploded rear perspective view of an eye shell of a binocular glare testing device for attachment to a phoropter, in accordance with one embodiment of the present invention.
FIG. 11 is a detailed rear elevation photographic view of an eye shell of a binocular glare testing device for attachment to a phoropter, in accordance with one embodiment of the present invention.

FIG. 10 is an exploded rear perspective view of an eye shell 6 of a binocular glare testing device for attachment to a phoropter, as shown in FIGS. 3 and 4. This Figure shows constituent portions of the eye shell 6, including aft sighting portion 32, main body portion 33, sight frame 34, frusto-conical light shade 35, and rear plate 36, assembled as shown about active sight axis 8. The lights may be incorporated using any physical arrangement so as to allow them to function for their purpose described herein. For instance, the lights may be provided in the form of an array of small bulbs disposed about the active sight path, or in the form of light emitting diodes that may be served by a circuit board incorporated into the eye cup, such as on by being placed on or incorporated into sight frame 34.

FIG. 11 is a detailed rear elevation photographic view of an eye shell or cup 6 of a binocular glare testing device for attachment to a phoropter, and using like reference numerals to those used with respect to FIGS. 4 and 5. This view shows the array of light emitting diodes 30 disposed about the active sight axis, and may be seen by the patient in using the device.

Figure 15:
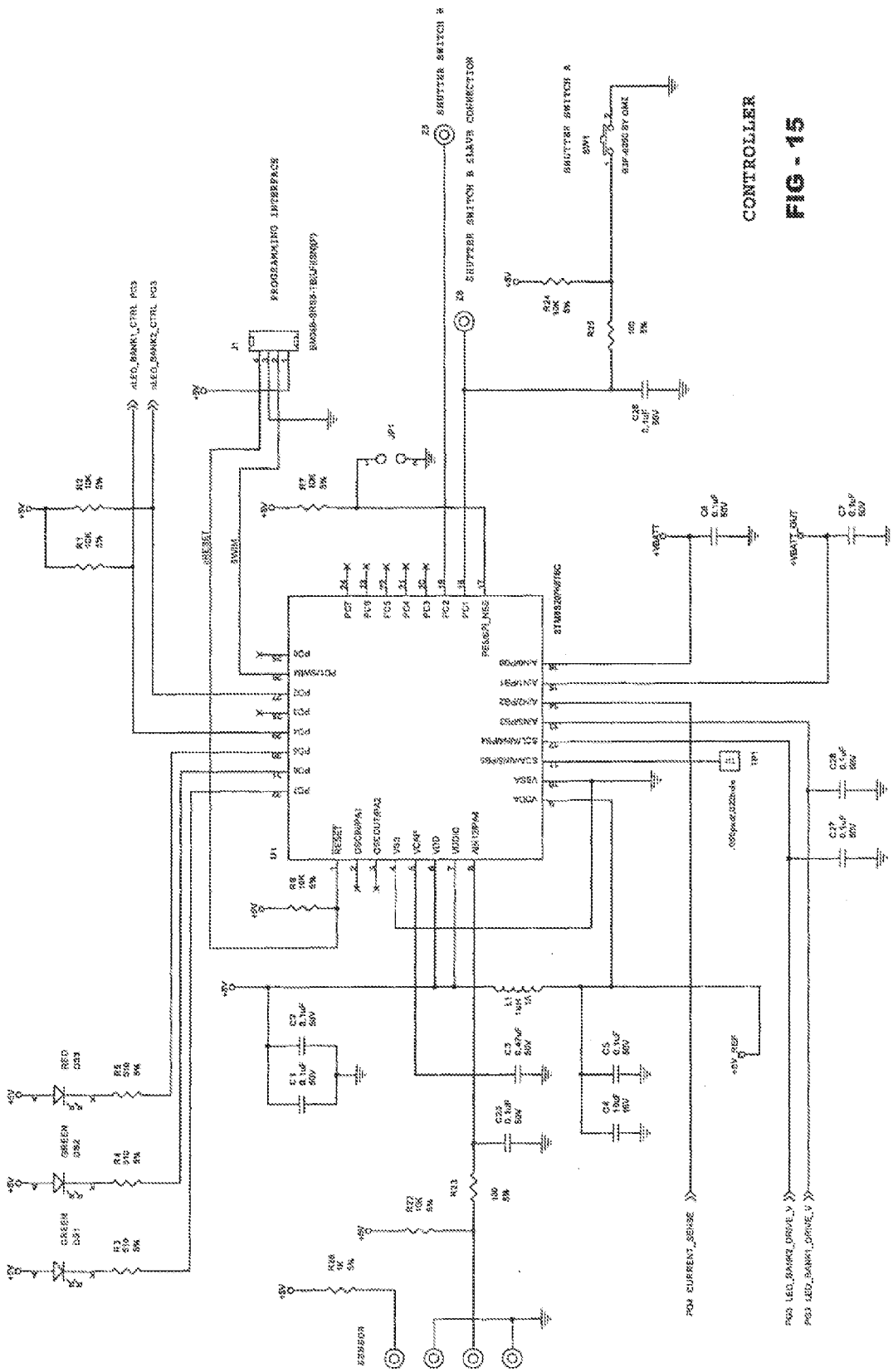
FIGS. 15-17 are circuit diagrams relating to the electronic controls for a light system that may be used in accordance with one embodiment of the present invention.
Figure 16:
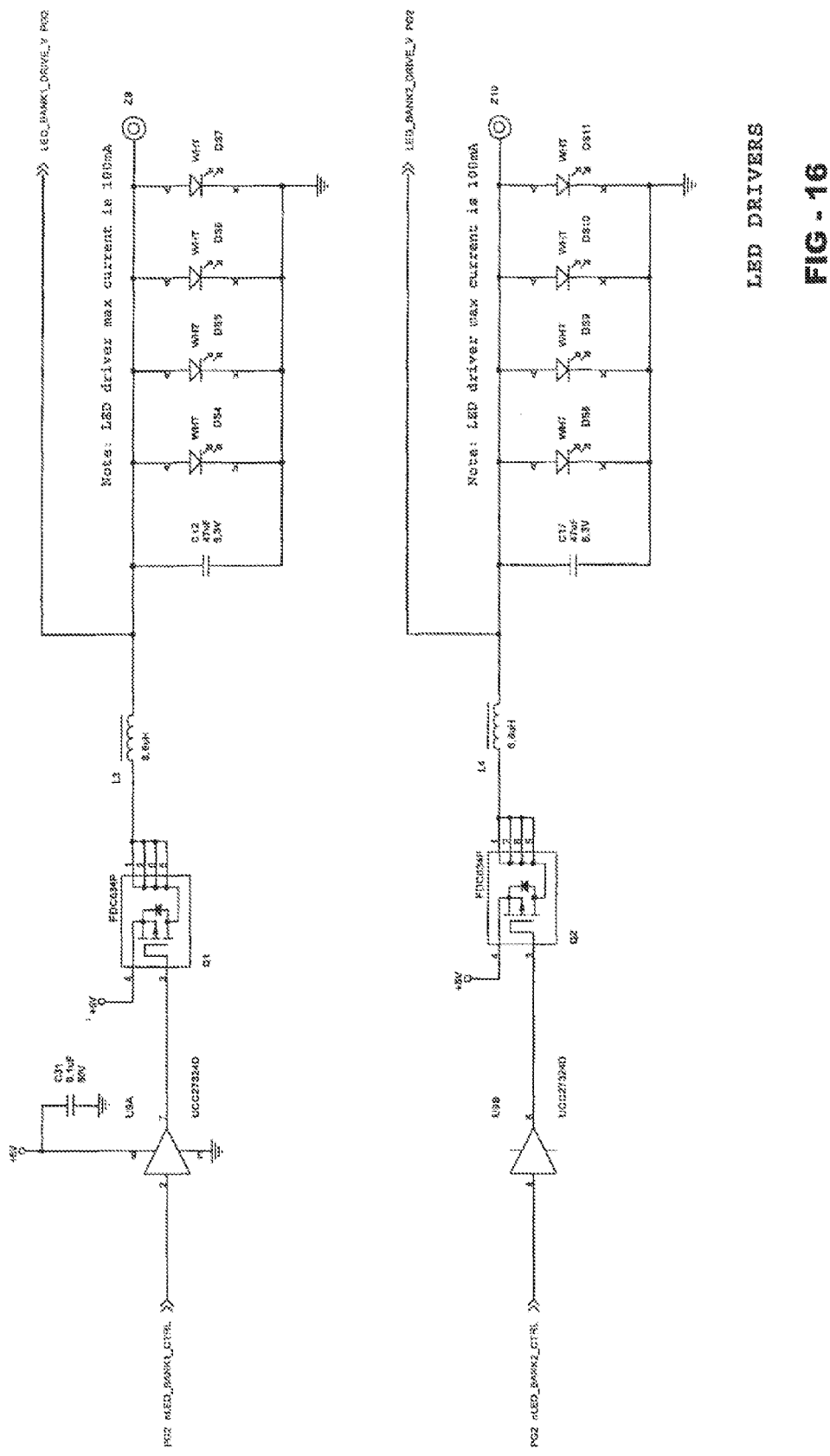
Figure 17:
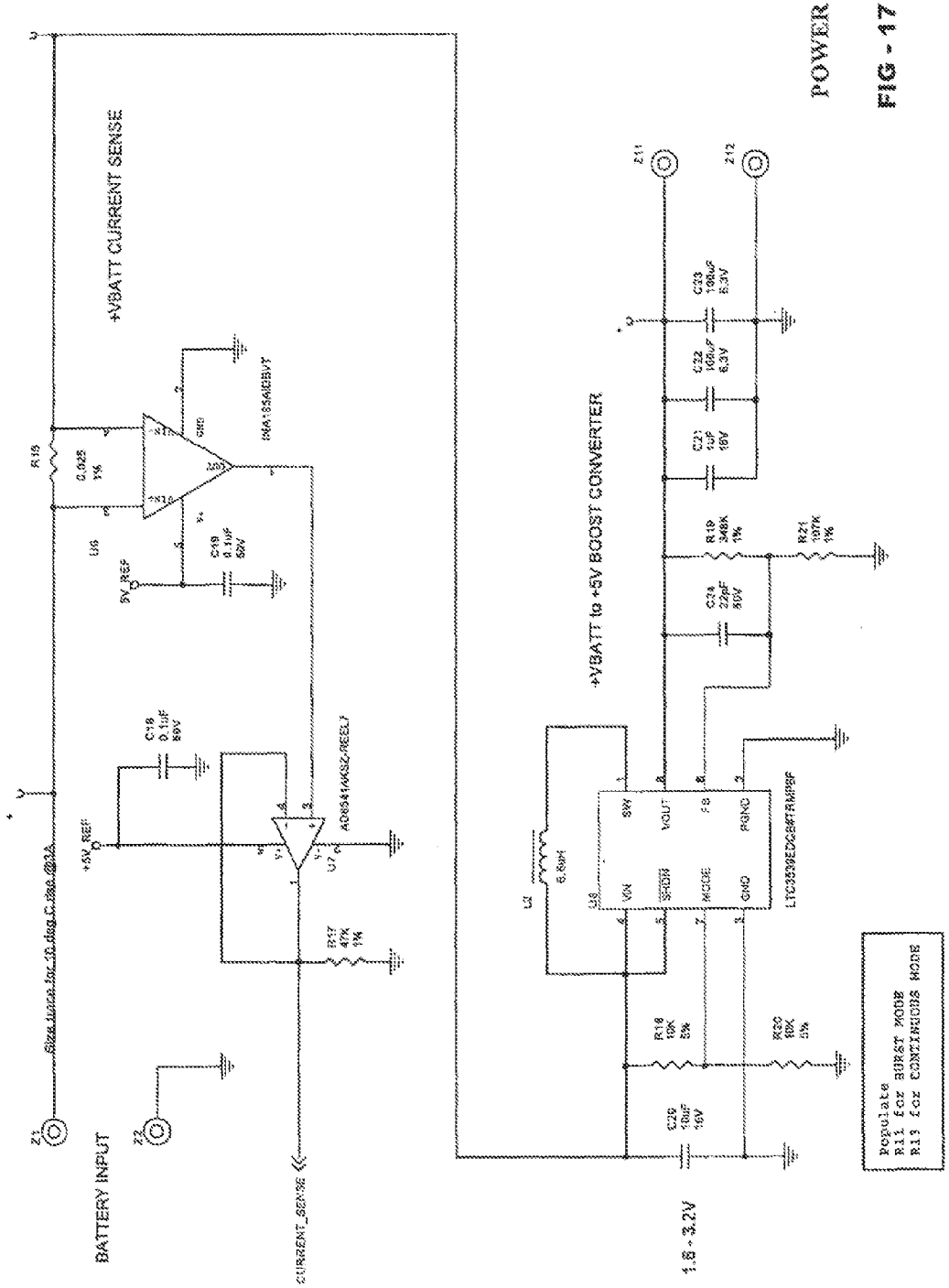

FIGS. 15-17 are circuit diagrams relating to the electronic controls for a light system that may be used in accordance with one embodiment of the present invention. FIG. 15 shows an example of the controller circuitry for an eye cup in accordance with a preferred embodiment of the present invention.

FIG. 16 shows an example of the circuitry for the LED drivers for an eye cup in accordance with a preferred embodiment of the present invention.

FIG. 17 shows an example of the circuitry for the power control, including the battery current sensor and the boost converter, for use in an eye cup in accordance with a preferred embodiment of the present invention.

In the preferred embodiment, the PCB dimensions may be as specified in the mechanical drawing. The board preferably has 4 layers, and the electronic components may be placed on both sides of the PCB, although components greater than >0.100 inch in height (excluding the LEDs) should only be placed on the primary side of the PCB. The LEDs preferably should be located on the secondary side of the PCB only (as specified in the mechanical drawing). It is also preferred that +5V, +5V_REF and GND_POWER should be a plane, and +VBATT and +VBATT_OUT can either be a trace or a plane. If a trace is used, the minimum preferred trace width should be 0.025 inch. Unless otherwise specified, the minimum signal trace width preferably is 0.006 inch. Typically, the primary and secondary sides of the PCB require a minimum 1 oz. copper thickness. The PCB solder mask should be blue while the PCB finish should be immersion gold for contrast. The finished PCB should be panelized for automated production. The preferred maximum acceptable panel size is 12"× 12".

Another variation may be in the form of an opera-glass type support, or in the form of a support bar supporting the pair of eye cups, at least one of the eye cups being moveably attached to the support bar so as to allow the distance between the pair of eye cups to be changed.

Figure 12:
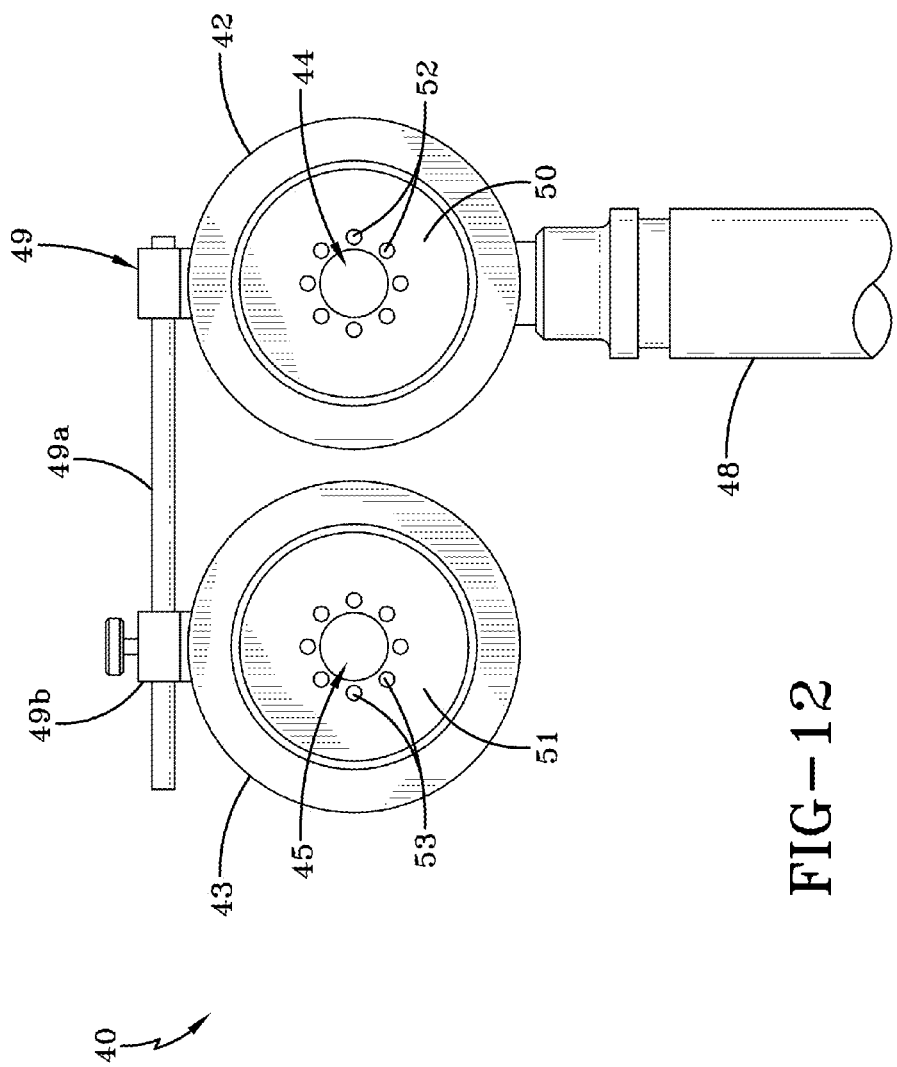
FIG. 12 is a rear elevation view of a portion of another binocular glare testing device, in the form of a hand-held device, in accordance with one embodiment of the present invention.
Figure 13:
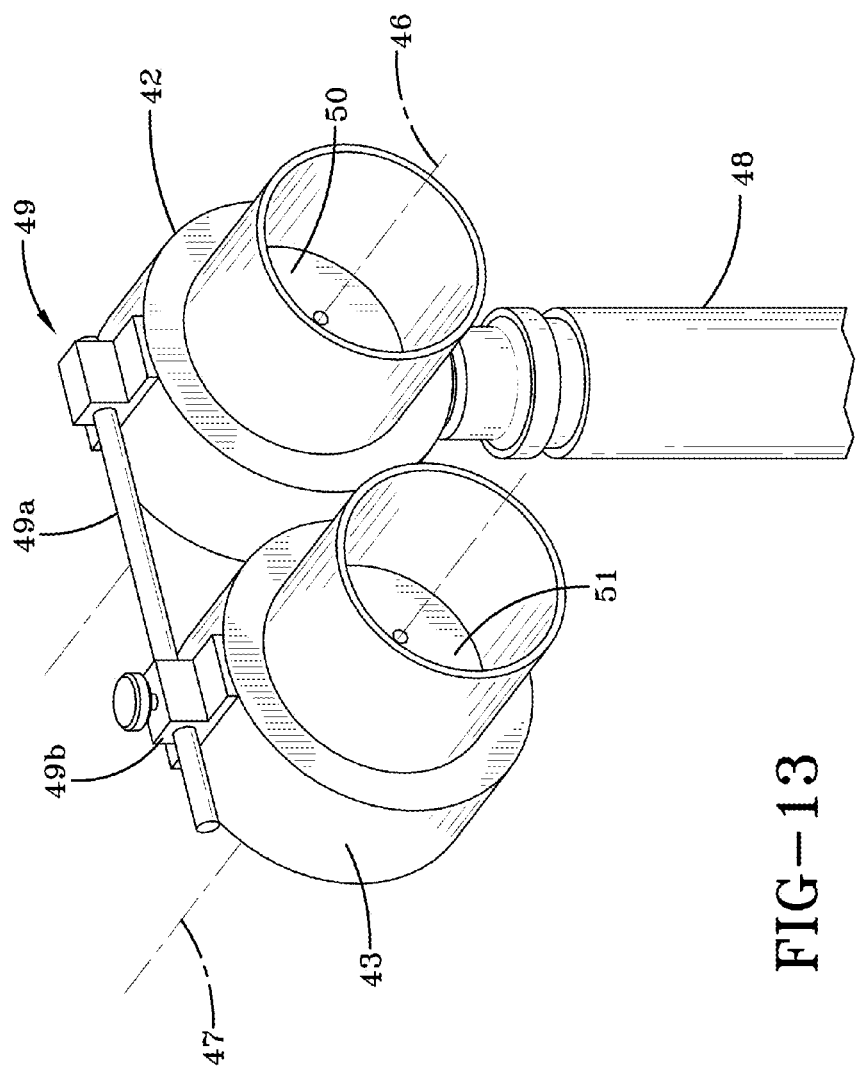
FIG. 13 is an upper rear perspective view of a portion of another binocular glare testing device, in the form of a hand-held device, in accordance with another embodiment of the present invention.
Figure 14:
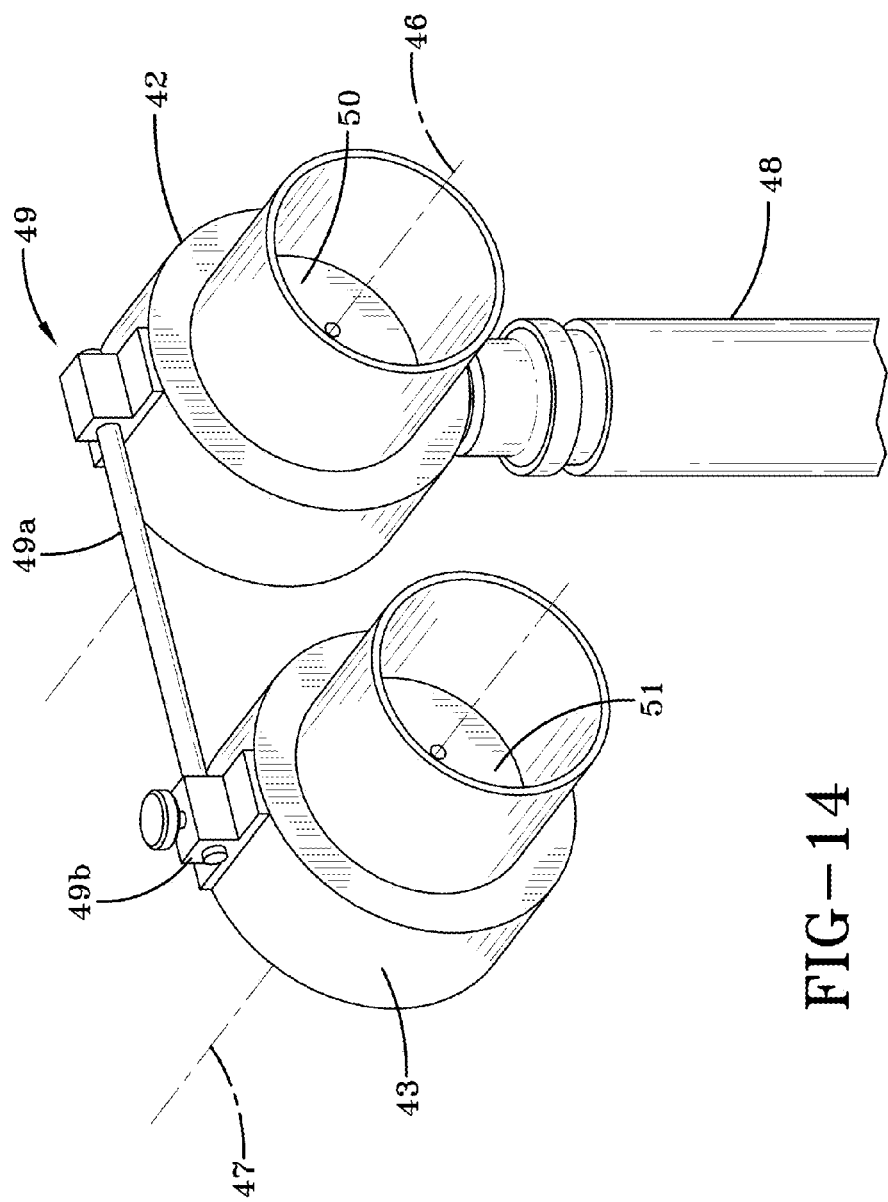
FIG. 14 is an upper rear perspective view of a portion of another binocular glare testing device, in the form of a hand-held device, in accordance with another embodiment of the present invention.

FIGS. 12, 13 and 14 are views of a portion of another binocular glare testing device, in the form of a hand-held device, in accordance with another embodiment of the present invention, wherein like reference numerals are used to indicate the parts and features thereof.

FIG. 12 is a front elevation view of a portion of a binocular glare testing device in an active position as applied to a hand-held device, in accordance with another embodiment of the present invention.

FIG. 12 shows a hand-held device 40 having a handle 48 and eye cups or shells 42 and 43 (such as those otherwise described with reference to FIGS. 1-8 and accompanying text) to be mounted as shown and defining respectively associated active sight apertures 44 and 45 and defining respective active sight axes 46 and 47 (as seen in FIGS. 13 and 14). The eye cups or shells 42 and 43 may be attached or supported in any way such as by having eye shell 42 attached to handle portion 48. This may be any attachment means that is consistent with the comfortable and accurate operation of the device, such as tension clamps, screws, hand screws, screw clamps, permanent or releasable adhesives, magnets, etc. Eye shell 43 may then be attached to eye shell 42 via adjustable support arrangement 49, so as to provide for adjustable support and allow adjustment and fixation of the interpupil distance. The adjustable support arrangement 49 may be in the form of an opera glass-style support rod 49a and moveable slide 49b which allows for adjustment and fixation of the eye cups or shells 42 and 43 with respect to one another. It will be appreciated that this type of arrangement may be used in association with any other binocular ophthalmic device, such as a phoropter, as described herein.

The eye cups or shells 42 and 43 may otherwise be attached through any other equivalent mechanical arrangement that will allow their repetitive and reliably accurate alignment and fixation of the active sight axes 46 and 47, such as through the use of binocular-type mechanical arrangements known and used in the art.

FIG. 12 also shows eye cups or shells 42 and 43 each comprising a wall partially enclosing a hollow interior chamber and having a viewing aperture defining a respective viewing line of sight axis for each eye cup, a portion 50 and 51, respectively, of each wall being provided with a plurality of lights 52 and 53, respectively, disposed around each the line of sight axis, as described herein, so as to provide a substantially isolated light box aligned with the active sight axes 46 and 47). In the preferred embodiment, a light source provides a ring of light about the aperture. The ring of light is provided near the aperture and preferably contiguous with the aperture so that the light source is close to the visual axis. The illustrated light source is a ring of LEDs located within the shell and about each aperture. It is noted however, that the light source can be of any suitable type and the light source can have any suitable configuration which provides a ring of light about the aperture and visual axis.

In a preferred embodiment, the binocular glare testing device according to the present invention may feature sight apertures that may be individually shuttered and/or adjustable. That is, the size of each aperture may be manually changed to a desired size. The illustrated aperture in eye cups or shells 42 and 43 may be constructed similarly to a camera aperture but it is noted that any suitable type of adjustable aperture can be utilized. For example, an adjustable aperture is available from the Merit Corporation of Schenectady, N.Y., which has a shutter type aperture which is adjusted by rotating an outer thumb wheel that may be adapted to the construction of this embodiment.

FIG. 12 also shows the handle portion 48 may contain a disposable or rechargeable battery pack to supply electric current to the light sources in the eye cups or shells 42 and 43 via electric conduits supplying eye cup or shell 42 through wires extending from the handle 48, and eye cup or shell 43 through wires extending from eye cup or shell 42 to eye cup or shell 43 via support rod 49a. The electric current to the light sources may be governed by an electric switch that may for instance, be placed in handle portion 48, such as thumb switches used for this purpose and known and used in the art (such as those used on commercially available devices, such as those available from Welch-Allen). Alternatively, the light sources in the eye cups or shells may be supplied with direct line current from a source in the examination suite, as convenient or required by the desired application, such as through AC line current supplied to the handle portion 48 and beyond, to service eye cups or shells 42 and 43.

FIGS. 13 and 14 are upper rear perspective views of a portion of another binocular glare testing device, in the form of a hand-held device, in accordance with another embodiment of the present invention; and using like reference numerals to those used with respect to FIG. 12. These Figures show the interpupil adjustment mechanism in a relatively narrow interpupil distance configuration, and in a relatively wide interpupil distance configuration, respectively.

The devices and systems of the present invention may be used as an attachment for a manual refractor and can be customized as an accessory for different original equipment manufacturers, or they may be directly incorporated into a phoropter system as an original equipment feature.

The present invention allows for the documentation of the amount of visual disability resulting from glare experienced by patients with mild to moderate cataracts. The devices and systems of the present invention are particularly useful in detecting visual impairment in night time conditions, such as by having a patient read a standard Snellen chart at the same time that a virtual image of a headlight would be illuminated through the eye piece. Glare may be tested by reference to the line acuity of the Snellen chart—a standard operating procedure in an eye care doctors' office.

In operating the apparatus and system of the present invention when used in association with a phoropter, the following steps are typically followed: (1) the patient is positioned in the active position of a phoropter so the patient may peer through the active sight channels defining the active sight axes; (2) the patient is presented with an eye chart (such as Snellen chart) or visual acuity testing chart or pattern; (3) the patient is asked to read or respond to the visual acuity testing chart or pattern to indicate perception or understanding to establish a base line acuity; (4) the lights are illuminated at times during the testing to assess the patient's visual acuity while under the influence of light impacting the eye at an angle and visual acuity testing is continued or repeated, preferably, for individual eye testing, by actuating a shutter or otherwise blocking one eye, while the other eye remains active in the acuity test. This may be done for instance by operating the shutter of the phoropter to conduct the acuity test under the influence of light only one eye at a time.

This method may be carried out through any combination of steps calculated to provide the desired glare testing of both eyes, either individually, sequentially or collectively.

The method may be carried out using other ophthalmic instruments, conventional or purpose designed, such as by using a binocular glare tester attachment of the present invention, which may include hand-held versions of the present invention, preferably incorporating shutters to allow individual or sequential glare testing on either eye.

The devices, systems and methods of the present invention thus allows for the convenient and effective measurement and documentation of glare disability without leaving the refracting lane, while allowing compatibility with a manual refractor for maximum efficiency. The present invention also permits high fidelity simulation of night-time driving conditions through the use of prescribed light wavelengths presented at an angle to the visual axis.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than the foregoing description, and all changes which come within the meaning and range of equivalency of the claims are intended to be embraced therein.

What is claimed is:

1. A phoropter comprising: a pair of eye cups, both said eye cups each comprising an opaque facing wall partially enclosing a hollow interior chamber and having a viewing aperture, said aperture defining a central viewing line of sight axis, and said opaque facing wall having a plurality of lights disposed radially around said central viewing line of sight axis.

2. The phoropter of claim 1, wherein said plurality of lights disposed around said central viewing line of sight axis so as to provide substantially uniform illumination about said central viewing line of sight axis.

3. The phoropter of claim 1, wherein each said opaque facing wall having said plurality of lights is non-reflective.

4. The phoropter of claim 1, said phoropter having respective lenses each defining a respective lens line of sight axis, and wherein said pair of eye cups are positioned so as to align said central viewing line of sight axes of respective said hollow interior chambers with respective lens line of sight axes of said phoropter.

5. The phoropter of claim 1, wherein said plurality of lights are arrayed radially about said central viewing line of sight axis so as to provide illumination within an angle of incidence of 10 to 25 degrees in relation to said central viewing line of sight axis.

6. The phoropter of claim 1, wherein said a plurality of lights are adapted to provide illumination with light of two different wavelength profiles.

7. The phoropter of claim 1, wherein said a plurality of lights comprise a first array adapted to provide illumination with light a first wavelength profile, and a second array adapted to provide illumination with light a second wavelength profile.

8. The phoropter of claim 7, wherein said first and second array of lights comprise a series of lights of different wavelength profiles placed in an alternating pattern around said line of sight axis.

9. The phoropter of claim 7, wherein said first array of lights and said second array of lights are provided with switches so as to be capable of being switched independently.

10. The phoropter of claim 1, wherein said plurality of lights comprise solid state light emitting diodes electrically connected to a boost converter.

11. The phoropter of claim 1, additionally comprising means for shuttering each said viewing aperture.

12. The phoropter of claim 1 wherein said means for shuttering said viewing apertures are adapted to shutter said viewing apertures optionally both separately or simultaneously.

13. The phoropter of claim 1, wherein said eye cups each comprise a lateral wall extending from said opaque facing wall so as to so as to provide a substantially isolated light box aligned with said central viewing line of sight axis.

14. A phoropter comprising: a pair of eye cups, both said eye cups each comprising an opaque facing wall partially enclosing a hollow interior chamber and having a viewing aperture defining a respective viewing line of sight axis, a portion of each of said walls being provided with a plurality of lights disposed around said line of sight axis, said pair of eye cups attached to said phoropter so as to allow adjustment of the distance between said pair of eye cups.

15. A phoropter of claim 14, wherein said phoropter has respective lenses each defining a respective lens line of sight axis, and wherein said mounting means attaches said pair of eye cups so as to align said viewing line of sight axes of said respective hollow interior chambers with respective lens line of sight axes of said phoropter.

16. A phoropter of claim 14, wherein said plurality of lights are arrayed about said line sight axis so as to provide illumination such that within an angle of incidence of the light is limited to 10 to 25 degrees in relation to the sight line axis.

17. A phoropter of claim 14, wherein said a plurality of lights are adapted to provide illumination with light of two different wavelength profiles.

18. A phoropter of claim 17, wherein said a plurality of lights comprise a first array adapted to provide illumination with light a first wavelength profile, and a second array adapted to provide illumination with light a second wavelength profile.

19. A phoropter of claim 18, wherein said first and second array of lights comprise a series of lights of different wavelength profiles placed in an alternating pattern around said line of sight axis.

20. A phoropter of claim 18, wherein said first array of lights and said second array of lights are provided with switches so as to be capable of being switched independently.

* * * * *